(12) United States Patent
Ostuni et al.

(10) Patent No.: US 8,901,179 B2
(45) Date of Patent: Dec. 2, 2014

(54) PROCESS FOR SYNTHESIS OF METHANOL

(75) Inventors: Raffaele Ostuni, Milan (IT); Ermanno Filippi, Castagnola (CH)

(73) Assignee: Casale SA (CH)

( * ) Notice: Subject to any disclaimer, the term of this patent is extended or adjusted under 35 U.S.C. 154(b) by 358 days.

(21) Appl. No.: 13/202,222

(22) PCT Filed: Mar. 8, 2010

(86) PCT No.: PCT/EP2010/052917
§ 371 (c)(1), (2), (4) Date: Aug. 18, 2011

(87) PCT Pub. No.: WO2010/102981
PCT Pub. Date: Sep. 16, 2010

(65) Prior Publication Data
US 2011/0301252 A1    Dec. 8, 2011

(30) Foreign Application Priority Data
Mar. 12, 2009  (EP) .................................... 09155045

(51) Int. Cl.
*C07C 27/00*     (2006.01)
*C07C 29/151*    (2006.01)

(52) U.S. Cl.
CPC .................................. *C07C 29/1518* (2013.01)
USPC ........... 518/705; 518/700; 518/702; 518/703; 518/704

(58) Field of Classification Search
USPC .......................................... 518/700, 702–705
See application file for complete search history.

(56) References Cited

U.S. PATENT DOCUMENTS 4,326,041 A * 4/1982 Bahnisch ...................... 518/702

FOREIGN PATENT DOCUMENTS

| GB | 2 087 867 A | 6/1982 |
| GB | 2 142 331 A | 1/1985 |

* cited by examiner

*Primary Examiner* — Jafar Parsa
(74) *Attorney, Agent, or Firm* — Akerman LLP

(57) ABSTRACT

A process for synthesis of methanol, where make-up syngas is reacted in a synthesis loop (10) obtaining crude methanol, and where a purge gas (20) taken from said synthesis loop is heated to 200-500° C. by indirect heat exchange with a high-temperature heat source, the heated purge gas (33) being expanded in a gas expander (34) to recover energy.

11 Claims, 2 Drawing Sheets

PROCESS FOR SYNTHESIS OF METHANOL

This application is a national phase of PCT/EP2010/052917, filed Mar. 8, 2010, and claims priority to EP 09155045.9, filed Mar. 12, 2009, the entire contents of both of which are hereby incorporated by reference.

FIELD OF THE INVENTION

The invention relates to a process and plant for synthesis of methanol. More in particular, the invention relates to energy recovery from the purge gas of the high-pressure synthesis loop.

PRIOR ART

Make-up synthesis gas for the production of methanol is usually produced by steam reforming of a suitable hydrocarbon-containing feedstock, for example natural gas. The make-up syngas is a mixture of carbon oxides (CO, $CO_2$) and hydrogen ($H_2$), usually at a pressure of around 20-40 bar. The steam-reforming can be performed with different configurations: non-limitative examples are: a stand-alone primary reformer; a primary reformer followed by a secondary reformer, possibly an auto-thermal reformer, or an auto-thermal reformer.

The make-up syngas is usually cooled to recover heat, and fed to a high-pressure (HP) synthesis loop with a multi-stage main compressor.

The reactions in the HP synthesis loop can be summarized as $CO+2H_2 \rightarrow CH_3OH$ and $CO_2+3H_2 \rightarrow CH_3OH+H_2$, where the reactants CO, $CO_2$ and $H_2$ are supplied by the make-up syngas. The hydrogen to carbon ratio (molar) of the make-up syngas is defined by the stoichiometric number R $$R = \frac{[H_2] - [CO_2]}{[CO] + [CO_2]}$$

and it is known that the kinetic of the reactions in the HP loop asks for an optimum R slightly greater than 2, preferably in the range 2.05 to 2.3, depending on the $CO/CO_2$ ratio. A higher or lower R means that the HP loop operates under its capability.

The make-up syngas delivered by the reformer(s) however can significantly deviate from said optimum value of R. In particular, a front-end based on a primary reformer produces a make-up syngas with a significant hydrogen excess, for example with R equal to 3 or above, which means a 50% excess or more. This excess hydrogen increases the energy input of the main compressor, and the overall flow rate through the HP loop, without taking part in the synthesis process. Hence, it can be stated that excess hydrogen in the make-up syngas has a negative effect on the energy balance and performance of the methanol plant. In particular, compression of the excess hydrogen in the main compressor is substantially a waste of energy.

At least a portion of the excess hydrogen is usually drawn from the synthesis loop, together with inerts, forming the so called purge gas stream. In the prior art, the purge gas is recycled as fuel for the reforming section. This energy recovery however does not compensate for the above drawbacks.

A known measure to mitigate the problem of excess $H_2$ in the make-up syngas is to add carbon dioxide to adjust the value of the stoichiometric number R. Carbon dioxide however is not always available. Carbon dioxide can be recovered from the flue gas of a reformer, but the process needs expensive equipment and a lot of energy. A conventional $CO_2$ recovery section for this purpose comprises an absorber tower where the flue gas are counter-currently washed with amine-based solution; a $CO_2$-rich solution is separated at the bottom of the tower and is purified in a regenerator, where reboilers supply heat to the solution in order to break the bound between the solution and the carbon dioxide; a $CO_2$-rich gaseus stream is separated at the top of the regenerator, compressed in a suitable compressor and recycled back to the primary reformer. Another measure is the installation of an oxygen-fired secondary reformer, but this component is also expensive.

SUMMARY OF INVENTION

The technical problem faced by the invention is to overcome the negative effect of the hydrogen excess in the make-up syngas on the overall energy balance.

The idea underlying the invention is to effectively recover the enthalpy of the purge gas by heating the purge gas by indirect heat exchange with a suitable high-temperature heat source which is made available by the process, and expand the heated purge gas in a suitable expander, to produce mechanical energy. Said mechanical energy, or portions thereof, can be used as such e.g. to drive a compressor, or converted into electric energy. The purge gas at the output of the expander can be further used as fuel.

Hence, the above technical problem is solved with a process for synthesis of methanol, where a hydrocarbon-containing feedstock is reformed obtaining a make-up synthesis gas containing carbon oxides and hydrogen, and said make-up syngas is reacted in a synthesis loop obtaining crude methanol, and where a purge gas containing hydrogen is taken from said synthesis loop, the process being characterized in that said purge gas is heated by recovering heat by indirect heat exchange with at least one high-temperature heat source of said process, and heated purge gas is expanded as such in a suitable expander, and energy is recovered from expansion of the purge gas through said expander.

The high-temperature heat source is any source adapted to heat the purge gas to a temperature greater than 200° C. and preferably greater than 350° C. A preferred range for heated purge gas is 200 to around 500° C. and more preferred 350 to 500° C. The purge gas can also be heated over 500° C. if a suitable heat source is available in the process. Pre-heating of the purge gas with low temperature source(s) which are available in the plant is also possible, for example using any source of waste heat such as condensing steam. The purge gas is preferably pre-heated to around 100-120° C. before it is heated to high temperature.

According to a first aspect of the invention, the purge gas is heated by heat exchange with the hot flue gas of the reforming process. In one embodiment of the invention, at least one step of the reforming process of the hydrocarbon-containing feedstock takes place in a primary reformer, and the purge gas taken from the synthesis loop is passed through a coil in the convective section of said primary reformer. Using the flue gas as heat source allows the purge gas to reach a temperature up to around 500° C. or above.

According to a second aspect of the invention, the purge gas is heated by heat exchange with hot steam, for example high-pressure superheated steam which is usually available in a methanol plant. Hot steam can be taken for example from a steam turbine driving the main compressor of the syngas. Use of hot steam as high-temperature heat source usually allows the purge gas to reach 320-380° C.

The flue gas heated embodiment generally achieves a higher temperature of the purge gas and then more power from the expander; the steam-heated embodiment generally reaches a lower temperature but, on the other hand, has the advantage that the purge gas heater is operationally independent from the reforming section. In other words, the energy recovery from the purge gas, in this embodiment, is smaller but has less influence on the heat balance of the reformer. This solution can be preferred to ensure stable and smooth operation of the reformer, for example because the purge gas flow rate is not constant and tends to increase e.g. due to aging of the synthesis catalyst and related loss of performance.

The choice of the preferred embodiment may also depend on the possibility to export the electric energy to a grid. The flue gas heated embodiment may be preferred when there is a demand of electric energy outside the plant, or the surplus of electric energy can be exported at attractive conditions.

According to another aspect of the invention, the purge gas taken from the synthesis loop is treated in a separator before the preheating step. Said treatment can serve to condition the purge gas and recover some useful such as methane or hydrogen. In one embodiment, some residual methane is separated from the purge gas in the form of a $CH_4$-rich gas stream which is recycled to the reforming step. In another embodiment, a $H_2$-rich gas stream is separated and recycled in the process.

The expander is preferably coupled to an electric generator delivering electric energy. Said electric energy can be used to feed the electric drives and auxiliaries of the methanol plant and/or exported. In a preferred embodiment of the invention, electric energy delivered by said generator is used to power the circulator of the HP loop, and the rest—if available—is exported. The mechanical energy delivered by the expander, or a part thereof, can be used directly to drive any suitable equipment such as a compressor. The expander is preferably a turbo-expander.

The purge gas is expanded as such, i.e. without a combustion process. Hence, said expander provides unfired energy recovery, by converting the pressure energy of the purge gas into mechanical energy. The efficiency of the recovery is increased by the prior heating step with a high-temperature heat source, which increases the enthalpy of the purge gas and then the amount of recoverable energy. The expanded purge gas at the outlet of said expander maintains its heat value and can be further used as a fuel.

The outlet pressure of the purge gas expander is preferably slightly over the pressure of the hydrocarbon feedstock fed to the reforming section. In preferred embodiments said outlet pressure is 1 to 5 bar and more preferably around 1.5 to 3 bar.

In a preferred embodiment of the invention, the purge gas is taken at around 85 bar and 45° C. and pre-heated with steam condensate; a portion of the methane contained in the purge gas is separated through a suitable separator and the methane-depleted purge gas at a pressure of around 40 bar is further preheated to around 100-120° C. by heat exchange with another low-temperature source; the stream is then heated to at least 200° C. by heat exchange with the high-temperature source; the heated purge gas then enters a turboexpander at around 35-40 bar pressure and exits at around 1.5-3 bar.

An aspect of the invention is also a plant for the synthesis of methanol, comprising a reforming section where a hydrocarbon-containing feedstock can be reformed obtaining a make-up synthesis gas containing carbon oxides and hydrogen, and a synthesis loop adapted to convert said make-up syngas into crude methanol, the plant comprising a purge line for drawing a purge gas containing hydrogen from said synthesis loop, the plant being characterized in that it comprises a high-temperature, heat-recovery purge gas heater; a purge gas expander fed with heated purge gas delivered by said heater, and means adapted to recover energy from expansion of the purge gas through said expander.

Said means to recover energy preferably include an electric generator driven by the expander. Direct use of mechanical energy however is also possible. The purge gas expander, in other embodiments of the invention, is directly coupled to a compressor providing most or all of its power, or is directly coupled to the circulator of the synthesis loop.

Another aspect of the invention is the revamping of a methanol plant, by adding at least the following items: a high-temperature purge gas heater; means feeding said purge gas heater with a heat source available in said methanol plant; a purge gas expander and means feeding said expander with heated purge gas delivered by said heater; means adapted to recover energy from expansion of the purge gas through said expander. The purge gas heater can be provided, according to preferred embodiments, in the form of a heating coil in a primary reformer, or a steam-heated heat exchanger, as above.

The main advantage of the invention is that the pressure energy of the purge gas is recovered in an effective manner. The recovered power is notable, due to high pressure and relevant flow rate of the purge gas. For example, in a 5000 MTD (metric tons per day) methanol plant, up to 15-20 MW electric can be recovered. Conditioning the purge gas prior to heating involves a pressure loss, but has the advantage that a useful stream can be recovered in the process, and also that the specific consumption for pre-heating the purge gas, in terms of kcal/h per kW electric, can be reduced. A specific example will be given in the detailed description.

The recovered mechanical and/or electric energy can be used in the same methanol plant to drive pumps, compressors, etc. . . . In a preferred embodiment, electric energy is used to drive the HP loop circulator with an electric motor rather than with a steam turbine. The electric drive requires no additional energy input because the electricity is self-produced in the same methanol plant.

It can be noted that the energy recover provided by the invention compensates for the energy consumption of the syngas compression step, due to excess hydrogen. The advantages of the invention will be more evident with the following detailed description of a preferred embodiment, presented as a non-limitative example.

DETAILED DESCRIPTION OF PREFERRED EMBODIMENTS

Figure 1:
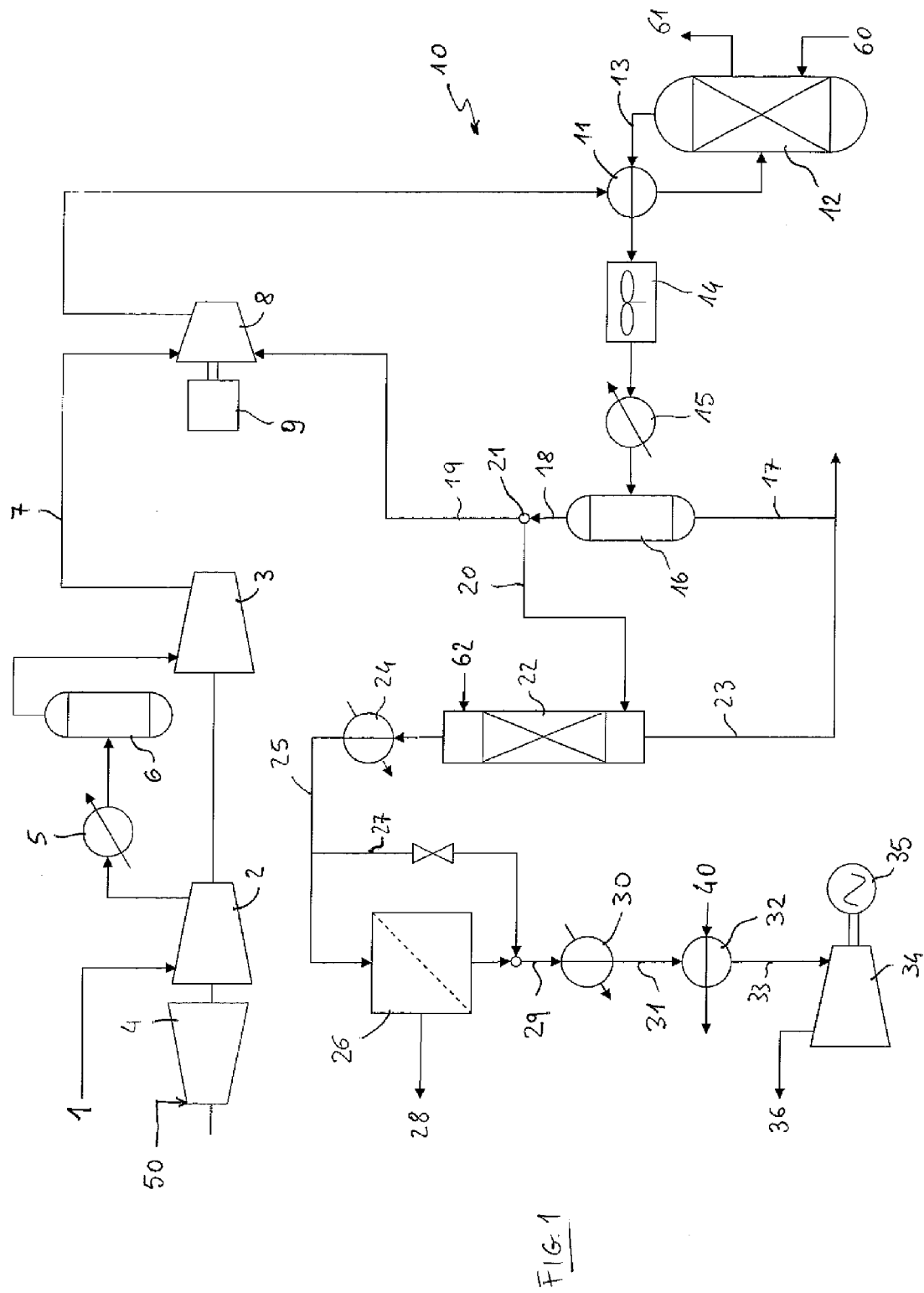
FIG. 1 is a simplified block diagram of a methanol plant according to one embodiment of the invention.

A make-up syngas 1 delivered by a reforming section (not shown) is compressed in a first stage 2 and second stage 3 of a main compressor, powered by a steam turbine 4. Intermediate cooling and separation of the liquid fraction are provided by a syngas cooler 5 and separator 6. The output 7 of the main compressor is sent to a high-pressure methanol synthesis loop 10, by means of a circulator 8 powered by an electric motor 9.

The make-up syngas is preheated in a recuperator 11 and feeds a synthesis reactor 12, where catalytic conversion into crude methanol takes place. The hot effluent 13 from said reactor 12 is cooled in the recuperator 11, air cooler 14 and water-cooled exchanger 15, and fed to a separator 16. Liquid crude methanol 17 is obtained at the bottom of this separator 16, while a gas stream 18 is obtained at the top of the same. Heat is removed from the reactor 12 by water 60 evaporating into steam 61.

A portion 19 of said effluent gas stream 18 is recycled to the circulator 8, while another portion 20 is the purge gas drawn from the HP loop 10. The portion 20 is usually a minor portion, for example 10%-20% of the total mass flow of stream 18. The portion is regulated preferably by a valve 21.

The purge gas 20 is treated in a washing column 22, to separate residual methanol in a stream 23 which is mixed with the crude methanol 17. Washing water 62 enters at the top of said column. The methanol-free purge gas recovered at top of column 22 is first pre-heated in a low-temperature heater 24, obtaining a stream 25 which is optionally treated in a separator 26 such as a membrane separator. A bypass 27 is also provided to control the flow rate through said separator 26.

The separator 26 yields a $CH_4$-rich stream 28 that is recycled to the reforming section, and a stream 29 of conditioned purge gas that is further pre-heated by indirect heat exchange in another condenser 30. The purge gas 31 at the output of said condenser 30 is then heated in a purge gas heater 32 at an appropriate high temperature, preferably to at least 200° C. The heated purge gas 33 is expanded in an expander 34 connected to a generator 35. The expander 34 is preferably a multi-stage turbo-expander. The expanded purge gas 36 at the output of said expander 34 is then recycled as fuel for the reforming section.

In one embodiment of the invention (FIG. 1), the purge gas heater 32 is realized as a coil in the convective section of a reformer of said reforming section producing the syngas 1. The purge gas 31 flowing in the tube side of said coil is heated by indirect heat exchange with flue gas 40 of said reformer.

In another embodiment (FIG. 2), the purge gas heater 32 is heated by hot steam. Referring to the figure, a portion 51 of the high-pressure steam input 50 of the turbine 4 can be deviated to said heater 32 or, as an alternative, a medium-pressure steam flow 53 can be drawn from the same turbine 4, e.g. downstream the first or an intermediate stage. Either the high-pressure flow 51 or medium-pressure flow 53 forms the hot steam input 54 of the purge gas heater 32. Steam 54 exits the purge gas heater 32 as condensate 55. Any suitable heat exchange unit can be used to exchange heat between the steam 54 and the purge gas 31; in a preferred embodiment, the purge gas 31 is preferably fed to the shell side of a shell-and-tube unit.

Figure 2:
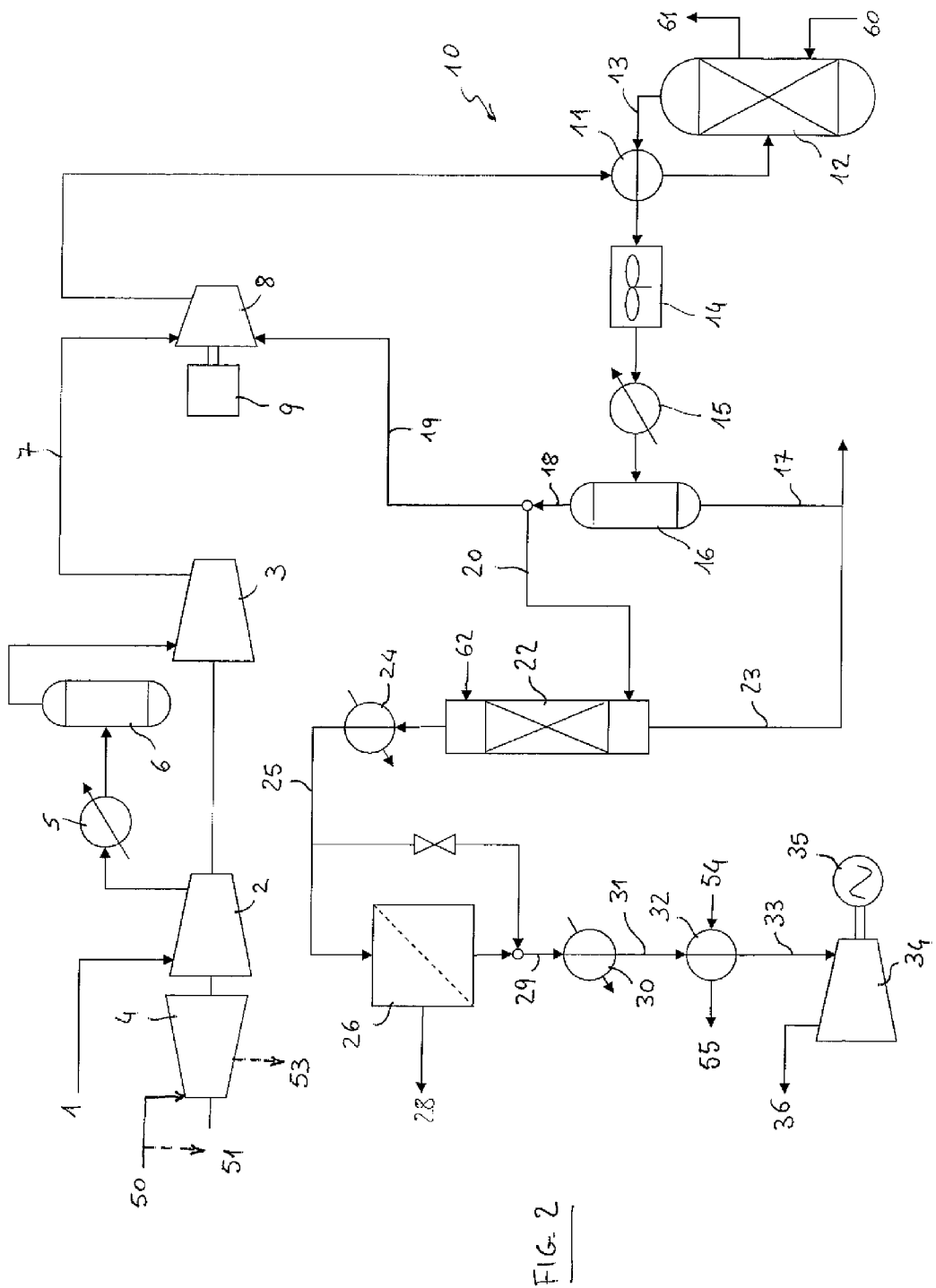
FIG. 2 is a scheme of another embodiment of the invention.

An advantage of the steam-heated embodiment of FIG. 2, as stated above, is that the operation of gas heater 32 is substantially independent from the reformer.

It should be noted that the purge gas 20 can be conditioned before the heating step in heater 32, for example removing water, carbon oxides and impurities. Conditioning of the flue gas may take place in the separator 26 and/or in further equipments. An advantage of conditioning the flue gas is that the specific heat consumption can be reduced. For example, the heating of unconditioned purge gas containing the usual percentages of methane, CO and $CO_2$, needs about 1078 kcal/h per kW electric, while purge gas deprived of $CH_4$ and carbon oxides would need about 980 kcal/h per kWel.

The invention achieves the above aims of improving the energy balance of the plant. In a typical situation, an energy saving about 3.0% is obtained. The energy consumption can be measured in terms of energy input (heat value of the feed) per tons of methanol produced. In an exemplificative 5000 MTD plant, heating of the purge gas to 360° C. and expansion in a turbo-expander lowers the consumption from 7.44 Gcal/ton to 7.31. Heating the purge gas to 500° C. by heat exchange with the primary reformer flue gas further lowers this figure to 7.257.

EXAMPLE 1

In a plant producing around 5000 MTD of methanol, the loop purge 20 is 9513 kmol/h at 84.2 bar (absolute) and 45° C. The molar composition of the purge gas is around 80% $H_2$, 15.4% methane and smaller amounts of nitrogen (2%) carbon oxides, residual methanol (<1%) and steam.

Residual methanol and methane are removed in the column 22 and separator 26, respectively. The methanol-free purge gas is heated to 90° C. in the first condenser 24 and enters the separator at 83.7 bar; the output of the separator is further preheated in the second condenser 30, obtaining the stream 31 at 115° C. and 39.7 bar pressure, comprising 86% hydrogen and 10.8% methane, plus nitrogen, carbon oxides and steam. The fictitious molecular weight of the conditioned purge gas 31 is 4.48.

Said stream 31 is heated to around 500° C. flowing in a coil of the convective section of the primary reformer of the plant. The input 33 of the expander 34 is 8046 kmol/h at 500° C. and 38.7 bar, while the outlet stream 36 is at 220° C. and 3 bar. The generator 35 delivers 19775 kW. The motor 9 demands 9000 kW, so a net electric output of 10775 kW is made available.

EXAMPLE 2

In the same plant of Example 1 above, the purge gas heater 32 is heated with high-pressure superheated steam 54 at 510° C., exiting the heater 32 as condensate 55 at 320° C. The purge gas inlet conditions of the expander 34 are 363° C. and 38.7 bar, while the outlet conditions are 127° C. and 3 bar. Hence, the electric output of generator 35 is slightly reduced to 16119 kW.

The invention claimed is:

1. A process for synthesis of methanol, where a hydrocarbon-containing feedstock is reformed obtaining a make-up synthesis gas containing carbon oxides and hydrogen, and said make-up syngas is reacted in a synthesis loop obtaining crude methanol, and where a purge gas containing hydrogen is taken from said synthesis loop, the process comprising the steps of:
   heating said purge gas by recovering heat with indirect heat exchange with at least one high-temperature heat source adapted to heat the purge gas to a temperature of at least 200° C., obtaining a heated purge gas;
   expanding said heated purge gas in a suitable expander; and
   recovering energy from expansion of the purge gas through said expander,
   wherein said high-temperature heat source is the hot flue gas of the reforming process converting the feedstock into said make-up syngas, or a flow of hot steam.

2. A process according to claim 1, said high-temperature heat source being adapted to heat the purge gas to a temperature in the range from 200° C. to about 500° C.

3. A process according to claim 1, where the purge gas is heated by passing through a coil in the convective section of a primary reformer.

4. A process according to claim 1, where the purge gas is conditioned prior to heating by said heat exchange with the high-temperature heat source.

5. A process according to claim 4, where the purge gas is conditioned by separating a $CH_4$-rich stream.

6. A process according to claim 4, where the purge gas is conditioned by separating a $H_2$-rich stream.

7. A process according to claim 1, where mechanical energy recovered from said expander is converted into electric energy, and at least a portion of said electric energy is used internally by the process to power electric drives and auxiliaries, and a remaining portion of said energy is exported.

8. A process according to claim 7, where said electric energy is used to feed a motor-driving a syngas circulator of said synthesis loop.

9. A process according to claim 1, where said expander is directly coupled to a compressor providing most or all of its power.

10. A process according to claim 9, where the expander is directly coupled to the circulator of the synthesis loop.

11. A method for revamping a plant for the synthesis of methanol, the plant comprising a reforming section where a hydrocarbon-containing feedstock can be reformed obtaining a make-up synthesis gas containing carbon oxides and hydrogen, and a synthesis loop adapted to convert said make-up syngas into crude methanol, the plant also comprising a purge line for drawing a purge gas containing hydrogen from said synthesis loop, the method comprising the steps of:
 adding at least a high-temperature purge gas heater;
 providing means feeding said purge gas heater with a heat source available in said methanol plant, said heat source being the flue gas of at least one reformer of said reforming section, or a flow of hot steam;
 providing a purge gas expander and means feeding said expander with heated purge gas delivered by said heater, and
 providing means adapted to recover energy from expansion of the heated purge gas through said expander.

* * * * *